United States Patent
Evdokimov et al.

[19]
[11] Patent Number: 5,861,029
[45] Date of Patent: Jan. 19, 1999

[54] HEART VALVE PROSTHESIS

[76] Inventors: Sergey V. Evdokimov, mk. 5, d.10 a/ya 716, 40056 Penza; Aleksandr P. Melnikov, Ul. Ternovskogo d.174 kv. 213, 440004 Penza, both of Russian Federation

[21] Appl. No.: 759,220

[22] Filed: Dec. 5, 1996

[30]     Foreign Application Priority Data

Feb. 14, 1996 [RU] Russian Federation ............. 96102902
Aug. 23, 1996 [EP] European Pat. Off. .............. 96113579

[51] Int. Cl.⁶ ....................................................... A61F 2/24
[52] U.S. Cl. ............................................. 623/2; 137/527.8
[58] Field of Search ............................... 623/2; 137/527.8

[56]           References Cited

U.S. PATENT DOCUMENTS

| | | |
|---|---|---|
| 4,274,437 | 6/1981 | Watts . |
| 4,276,658 | 7/1981 | Hanson et al. . |
| 4,308,624 | 1/1982 | Klawatter . |
| 4,451,937 | 6/1984 | Klawitter ...................................... 623/2 |
| 4,676,789 | 6/1987 | Sorenson et al. ............................ 623/2 |
| 4,689,046 | 8/1987 | Bokros . |
| 4,863,459 | 9/1989 | Olin . |
| 5,116,366 | 5/1992 | Hwang .......................................... 623/2 |
| 5,197,980 | 3/1993 | Gorshkov et al. . |
| 5,693,090 | 12/1997 | Unsworth ..................................... 623/2 |

FOREIGN PATENT DOCUMENTS

| | | |
|---|---|---|
| 0327790 | 8/1989 | European Pat. Off. . |
| 0403649 | 12/1990 | European Pat. Off. . |
| 95/28898 | 11/1995 | WIPO . |

*Primary Examiner*—Paul B. Prebilic
*Attorney, Agent, or Firm*—Rothwell, Figg, Ernst & Kurz

[57]           ABSTRACT

A heart valve prosthesis includes an annular body, a support having an upstream support surface, a downstream support surface and a side surface facing the central axis of the annular body, and leaflets mounted within the annular body so as to pivot between a closed position in which the blood backflow is restricted and an open position which allows the passage of the direct blood flow. Each leaflet has a contact surface cooperating with the contact surface of the other leaflet in the closed position, an outer side surface, an upstream surface, a downstream surface and support portions respectively interacting with the downstream support surface and the upstream support surface of the support of said annular body. At least one portion of the outer side surface of at least one of the leaflets is formed such that a clearance is provided between the portion and the side surface of the support means of the annular body and at the portion a downstream projection and an upstream projection are provided, the upstream surface of the downstream projection and the downstream surface of the upstream projection forming the support portions.

5 Claims, 3 Drawing Sheets

HEART VALVE PROSTHESIS

The invention relates to a heart valve prosthesis comprising an annular body having an upstream end surface facing the direct blood flow, a downstream end surface facing the blood backflow, an inner surface and an outer surface, support means having an upstream support surface, a downstream support surface and a side surface facing the central axis of said annular body, and leaflets mounted within said annular body so as to pivot between a closed position in which the blood backflow is restricted and an open position which allows the passage of the direct blood flow, each leaflet having a contact surface cooperating with the contact surface of the other leaflet in the closed position, an outer side surface, an upstream surface, a downstream surface and support portions respectively interacting with said downstream support surface and said upstream support surface of said support means of said annular body.

The problem of creating heart valve prostheses capable of providing satisfactory substitutes for natural heart valves of humans damaged by congenital or acquired pathology have a history of more than 30 years.

During this long period many designs of heart valve prosthesis have been developed and tried, which function like a check valve ensuring direct blood flow when the closing element is in the opened position and preventing blood backflow when the closing element is in the closed position.

Due to their excellent hemodynamic parameters and the provision of central practically laminar flow the most commonly accepted valves in cardiac surgery today are the valves, which have a closing element comprising two semicircular leaflets hinged to the body of the prosthesis while the hinge elements are either a projection on the body and a slot (recess) in the leaflet, e.g. U.S. Pat. No. 4,863,459, or a recess in the body and a projection on the leaflet, e.g. U.S. Pat. No. 4,276,658 or U.S. Pat. No. 4,689,046.

The main differences in the constructions of such heart valve prostheses are connected with efforts to overcome the problem of thrombus formation at the prosthesis. In order to decrease the risk of thrombus formation one has to eliminate blood stagnation zones, ensure laminar blood flow and provide good washing of all elements of the valve.

An attempt to prevent thrombus formation at the implanted heart valve prosthesis has resulted in a heart valve prosthesis according to U.S. Pat. No. 4,308,624 having an annular body inside which there is a closing element connected to the body through a means for turning said closing element from a closed position to an open position, and vice versa. The closing element comprises two arcuate leaflets. The downstream surface of each leaflet facing the backflow of blood is curved concave when the closing element is in a closed position.

The inner surface of the valve body is cylinder-shaped, its portion facing the direct blood flow having a smaller diameter than its other portion facing the backflow of blood. The meeting zone of these two portions serves as the valve seat. Two diametrically opposite flat portions run through the entire height of the valve body.

Each leaflet is connected to the valve body by a hinge mechanism. The hinge mechanism comprises two cooperating elements, one of which is located on the flat portions of the inner surface of the valve body while the other is located on the opposite sides of the closing element.

The element of the hinge mechanism located on the flat portions of the inner surface of the body is shaped as two oblong recesses which axes make up an angle of 20 degrees with the diametral plane of the body. The element of hinge mechanism located on the opposite sides of the closing element is shaped as spherical projections which engage the recesses located in the inner surface of the valve body and cooperate by their support surfaces with the support surfaces of the recesses.

When the valve opens the leaflets pivot in the hinges moving from a closed position to an open position. Due to the downstream concave surfaces of the leaflets a channel is created between the leaflets for passage of the direct blood flow. Hydrodynamic studies have shown that the structure of the direct blood flow between the leaflets is not homogeneous. Though in the plane running through the central axis of the body parallel to the flat portions of the body the blood flow is practically laminar and fills the whole section of the valve, yet in the plane perpendicular to the flat portions of the body a laminar flow exists only in the central part of the heart valve and there is a large blood stagnation zone in the hinge regions.

When the valve closes the leaflets pivot in the hinges moving from an open position to a closed position. During this action they interact with the valve seat located on the inner surface of the valve.

The absence of washing by blood flow in regions adjacent to hinges leads to higher risks of thrombus formation exactly at these places. The movement of leaflets along the blood flow during their opening and closing in oblong recesses does not solve the problem of thrombus formation because it does not eliminate stagnation zones and does not provide adequate washing of hinge mechanism. In addition the hinge in the form of a recess and projection that engages this recess does not reduce their thromboresistance but subjects the elements of blood to further damage when they are caught between the interacting friction surfaces of the recess and the projection.

An attempt to eliminate the above mentioned inadequacies was made with the heart valve prostheses which embody one common idea i.e. the realization of rotation of leaflets around the central axis of the valve body. In particular, in the heart valve prosthesis of U.S. Pat. No. 4,274,437 leaflets of the prosthesis are connected to the valve body by means of hinges, the hinge elements of which are projections on the opposite sides of the leaflets that engage the recess in the inner surface of the valve body running along the entire periphery. In the heart valve prostheses of U.S. Pat. No. 5,197,980 or EP O 403 649 B1 the hinge elements are slots (recesses) located on the opposite sides of the leaflets that engage the annular projection on the inner surface of the valve body.

The heart valve prosthesis according to EP O 327 790 B1 is the closest one to the prosthesis of the present invention and considered as generic kind. The indicated prosthesis comprises an annular body intended to be traversed by the blood and two leaflets mounted within the body so as to to able to pivot between an open position in which the leaflets allow the blood to pass freely through the body in direct direction, and a closed position in which the leaflets jointly prevent the blood from passing through the body in the opposite direction. The leaflets have the upstream surface facing the direct blood flow and the downstream surface which is concave and faces the backflow of blood.

The hinge mechanism that holds the leaflet within the valve body has two recesses located at the opposite sides of the leaflet, and an annular projection located around the entire periphery of the inner surface of the valve body.

During the valve opening the leaflets interact between themselves pivoting around the body projection and move into the open position.

During the valve closing the leaflets pivoting around the body projection interact by their downstream surface with the support surface of the projection and seal the valve.

During the movement of the leaflets from the open position into the closed one and vice versa, the leaflets have the possibility to rotate around the central axis of the valve body. This shall provide the movement of the stagnation zone along the periphery of the body and the elimination of constantly localized zones susceptible of thrombus formation. Provision of the hinges in the form of a projection on the body and recesses in the leaflets reduces the friction surfaces and improves the washing of the elements of the hinge by blood flow.

However, there are no design elements that ensure compulsory rotation of the leaflets around the central axis of the valve body. Thus, it is very likely that such rotation will be contingent or will not happen at all. So the stagnation zones at the hinges will be localized and they will not be washed neither by the direct blood flow, nor by the blood backflow. Moreover, the projection at the inner surface of the valve body reduces the cross-section area of the valve orifice and contributes to the disturbance of the blood flow causing an increase of hydrodynamic resistance of the valve and an activation of the processes of thrombus formation.

It is the problem underlying the invention to create a heart valve prosthesis comprising a hinge mechanism that holds the leaflets within the valve body in such a way that for preventing thrombus formation localized stagnation zones inaccessible to blood washing are eliminated, while further improving the hemodynamic characteristics of the heart valve prosthesis and prolonging its lifetime.

This problem is solved according to a first aspect of the invention by a heart valve prosthesis of the generic kind, wherein at least one portion of the outer side surface of at least one of said leaflets is formed such that a clearance is provided between said portion and said side surface of said support means of said annular body and at said at least one portion a downstream projection and an upstream projection are provided, the upstream surface of said downstream projection and the downstream surface of said upstream projection forming the support portions.

Provision of the new hinge connection in the heart valve prosthesis in the form of projections at the leaflets and locating of the annular element of the body between them provides a limited backflow through clearances between said portions of the outer side surface of the leaflets and the inner surface of the annular body. This limited backflow washes out adherent blood elements at the place of the leaflet hinge connection with the body and prevents thrombus formation at the heart valve elements. In addition, the jets of the backflow originating between said portions of the side surface of the leaflets and the inner surface of the annular body and directed in a certain way rotate a part of the blood located below the upstream end surface of the annular body thus eliminating blood stagnation zones and providing a washing effect before the prosthesis.

It is recommended to provide said element of the body along the entire periphery of the annular body. In such a case the leaflets obtain an additional degree of freedom, that is the possibility to rotate around the central axis of the annular body. As a result, the rotating blood part action due to the influence of said jets of blood backflow, located from the side of the upstream end surface of the annular body provides stable compulsory rotation of the leaflets around the central axis of the annular body in a required direction.

The stagnation zone adjacent to the hinges shall be washed by the blood backflow through the clearances between the side surface of the leaflet and the inner surface of the body as well as by the direct blood flow when the leaflet rotates around the central axis of the body.

The location of said body element on the upstream end surface of the body reduces leaflet exposure relative to the downstream end surface of the body when the leaflets are in the open position, thus reducing the risk of their contact with surrounding heart structures which could lead to a jamming of the leaflets in their open position.

In case when heart valve prosthesis is used for patients with a small ventricle or there are some other ventricular obstacles that might impede a leaflet rotation around the central axis of the annular valve body, it is better to make said body element in the form of two protrusions located at diametrically opposite portions of the upstream end surface of the body so that the side surfaces of said body element face each other and their projections on the plane perpendicular to the central axis of the annular body are in fact the arcs of the circumference with a centre located on the central axis of the annular body and the upstream support surfaces of each body element must have stops at their ends for being able to interact with respective leaflet projections. The length of the upstream support surface of said body element, limited by said stops, should be from 0.05 to 0.25 of the length of the inner surface of the annular body.

In such a construction arrangement of a heart valve prosthesis the leaflets are also connected to the valve body by the hinge mechanism, elements of which are the projections on the leaflets locating between them said body element in the form of two stepped protrusions on the upstream end surface of the valve body. They also have an additional degree of freedom and can rotate around the central axis of the annular body, not a full turn but only in an oscillating movement. With such movement, the hinge mechanism zone also moves but the amplitude of this movement is limited by the stops on the upstream surface of said body element. Surgeon gains the possibility to orientate the prosthesis in the ventricle in such a way as to avoid an open leaflet contact with surrounding heart structures.

In order to provide the compulsory oscillating movement of leaflets around the central axis of the body, the downstream support surfaces of each protrusion located on diametrically opposite portions of the upstream end surface of the body should be made in such a way so that their logitudinal axes are at an angle relative to the central axis of the body and for the surfaces located on the opposite protrusion the angle modulus is equal but with the opposite sign. In such a construction arrangement of a heart valve prosthesis the downstream support surfaces of the protrusion located on the upstream end surface of the body form a slanting surface relative to the movement direction of the blood backflow and due to blood pressure on closing leaflets, they somewhat skid along the slant downstream support surface in one direction and due to the forces of the rotating part of the direct blood flow the opening leaflets turn in the opposite direction. The turn of the leaflets as a result of this oscillating movement is limited by the stops located on the ends of the upstream support surfaces of said annular body element.

The above-mentioned problem is solved according to a second aspect of the invention for improving the hemodynamic characteristics by a heart valve prosthesis of the generic kind wherein at least one portion of the outer side surface of at least one of said leaflets is formed such that a clearance is provided between said portion and said side surface of said support means of said annular body, at said at least one portion a support portion interacting with the upstream support surfaces of said support means is formed, and said support means is arranged at said upstream end surface of said annular body so that said downstream surface of said support means is situated at the same level or upstream of said downstream end surface of said annular body.

In such a construction arrangement of the heart valve prosthesis, said body element used for the connection of the leaflets is located outside of the hydraulic orifice of the body. Thus there is the possibility to make it in such a way as to minimize reduction of the effective area of the hydraulic orifice of the body and effects of said element on the blood flow.

It is recommended to make at least part of the inner surface of the annular body located from the side of direct blood flow in the form of a confuser surface with which the projections interact which are located on portions of the side surface of the leaflets having a clearance relative to the side surface of said body element and with the arc radius of the side surface of said body element being equal or greater than the radius of the inner surface of the annular body.

In such a construction arrangement of the prosthesis, said body element does not protrude inside the body, so there is no reduction of the effective area of the orifice, hence there are lower energy losses during the passage of direct blood flow and better hemodynamic characteristics of the heart valve prosthesis.

It is expedient that each leaflet has two portions of outer side surfaces made with a clearance relative to the side surface of said body element located on the opposite sides of the outer side surface, each of them having at least two said projections. One of these projections interacts by its support portion on the upstream surface with downstream support surface of said body element, while the other interacts by its support portion on the downstream surface with the upstream support surface of said body element. The support surfaces located on said leaflet projections and interacting with the support surfaces of said body element are made convex.

Provision of the portions on the opposite sides of the outer side surface with a clearance relative to said body element enables washout of adherent blood elements from each zone where a leaflet is hinged to the body. Provision of projections on these portions enables not only retaining and pivoting of the leaflet within the body but also fixing of the clearance between the side surface of the leaflet and the inner surface of the body which determines the rate of blood backflow that washes the hinge adjacent zone.

Provision of convex support surfaces of said leaflet projections which interact with the support surfaces of said body element, enables rolling friction interaction between them which ensures minimal wear out of the interacting surfaces and increases the reliability and lifetime of the heart valve. In addition this prevents a trauma of the formed blood elements.

The above-mentioned problem is solved according to a third aspect of the invention aiming at increasing the thromboresistance by a heart valve prosthesis of the generic kind wherein at least on one of said leaflets a channel is provided, the surface of the channel crossing the contact surface of said leaflet to allow a restricted blood backflow when the leaflets are in the closed position.

In such a construction arrangement of the prosthesis, the limited blood backflow, passing through said channel, washes those zones of the valve surfaces where a higher probability of the adhesion of the formed blood elements exists.

It is expedient that each leaflet has at least one said channel in order to allow a limited blood backflow. Said channel is located at one side of the outer side surface and is restricted from one side by the inner surface of the annular body and at the same time total area of said channels for the passage of blood backflow and the clearances between the outer side surface and the inner surface of the body and the side surface of said body element should be from 0,2 to 8% of the orifice area of the body.

In such a construction arrangement of the prosthesis the backflow washes not only the downstream surface of the leaflets but also the interacting surfaces of said body element and of the projections on the side surface of the leaflets. In addition the stream of the blood backflow reaches the surfaces of the body and washes the threads of fibrin away which could spread from the sewing ring to the side surface of the leaflets.

The optimum rate of the limited backflow is reached when this flow is strong enough, but the volume of blood passing back should not exceed 20% of the volume of blood passing through in direct direction, otherwise the energy losses at the valve are considered to be unacceptably high. In order to obtain the optimum rate of blood backflow it is necessary that the aggregate area of said channels should be within 0.2 to 8% of the area of the body orifice.

The heart valve prosthesis, made according to the invention, allows to reduce the probability of thrombus formation, has improved hemodynamic characteristics and higher reliability of valve construction. It finds most utility when applied for replacement of degenerative natural aortic and mitral heart valves in humans, and will meet equal success when used for replacing a damaged tricuspid valve.

In the following embodiments of the invention are described by means of the accompanying drawings, wherein FIG. 1 is an enlarged view of a first embodiment of a heart valve prosthesis with its leaflets in a closed position as viewed from the downstream side with respect to the direct blood flow;

Figure 2:
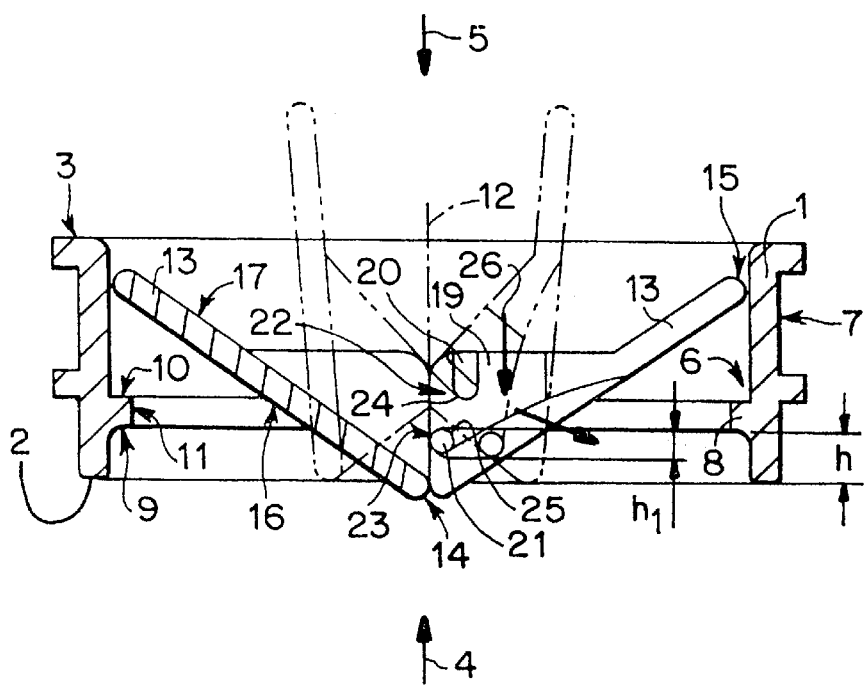
FIG. 2 is a partly sectional view taken along lines II—II of FIG. 1.
Figure 4:
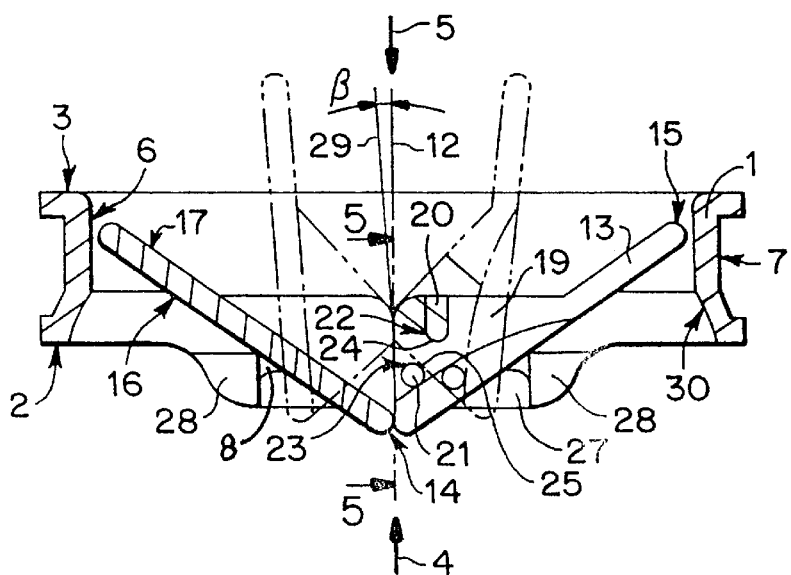
FIG. 4 is a partly sectional view taken along lines IV—IV of the heart valve of FIG. 3 in a closed position.
Figure 7:
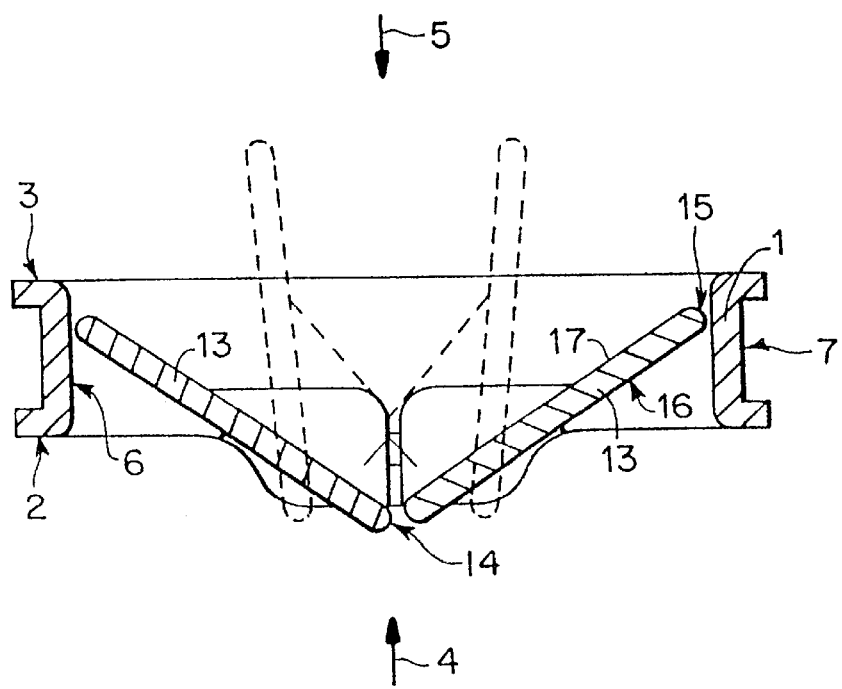
FIG. 7 is a partly sectional view taken along lines VII—VII of FIG. 6.

In FIG. 2, FIG. 4 and FIG. 7 broken lines are used to show the leaflets in the open position.

The heart valve prostheses shown in FIGS. 1 to 7 are used for replacement of diseased natural aortic or mitral heart valves.

Figure 1:
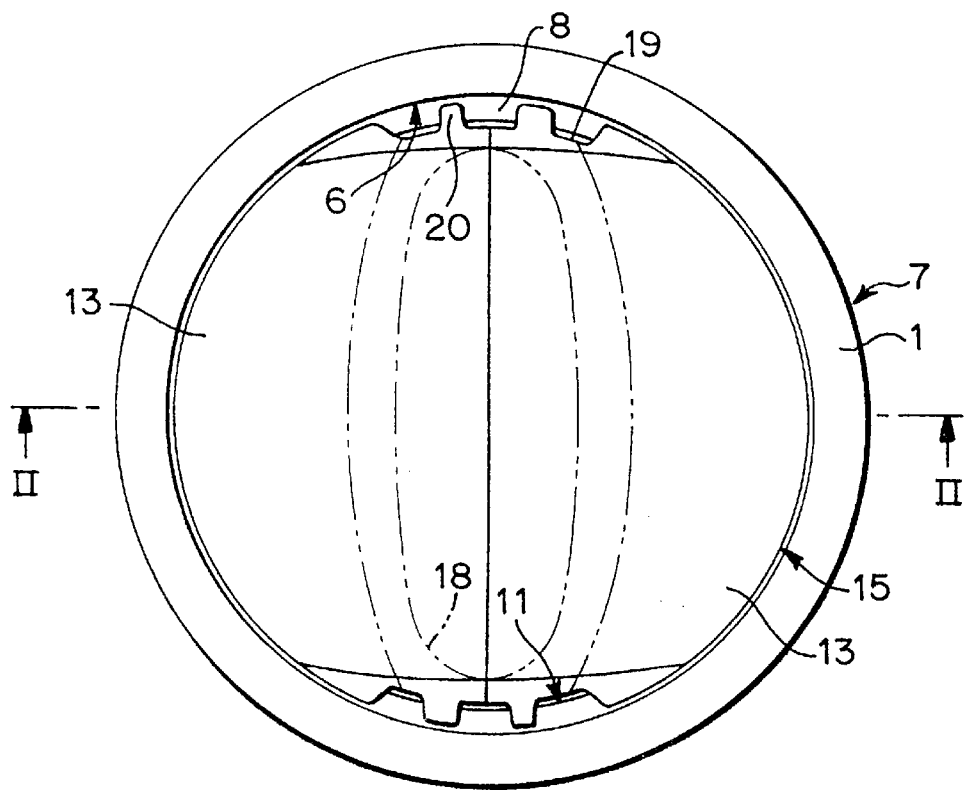

The first embodiment of the heart valve prosthesis shown in FIG. 1 and FIG. 2 comprises an annular body 1, having an upstream end surface 2 and a downstream end surface 3, facing the direct blood flow 4 and the blood backflow 5, respectively, an inner surface 6 and an outer surface 7. In the interior of the annular body 1 an annular flange 8 is provided having an upstream support surface 9, a downstream support surface 10, and a side surface 11, facing the central axis 12 of the annular body 1. The annular flange 8 runs along the entire periphery of the innner surface of the annular body 1.

Within the annular body 1 two leaflets 13 are mounted pivotable between a closed position in which the blood backflow 5 is restricted and an open position which enables the passage of the direct blood flow 4. Each leaflet 13 comprises a contact surface 14 cooperating with the contact surface of the other leaflet in the closed position, an outer side surface 15, an upstream surface 16 and a downstream surface 17. A portion 18 of the downstream surface 17 of each leaflet 13 is formed concave to allow the passage of the direct blood flow 4 between the leaflets 13 when they are in the open position.

The outer side surface 15 of each leaflet 13 comprises two portions 19 arranged with clearance relative to the side surface 11 of the flange 8 of the annular body 1 and located on the opposite sides of the outer side surface 15 of each leaflet 13.

Each portion 19 comprises an upstream projection 20 and a downstream projection 21 the space therebetween being limited by an upstream support surface 22 and and a downstream support surface 23 forming support portions 24 and 25, respectively, which interact with the downstream surface 10 and the upstream surface 9 of the flange 8 of the annular body, respectively. The support portions 24 and 25 are smoothly convex. The distance "h" of the upstream support surface 9 of the flange 8 from the upstream end surface 2 is greater than the axial dimension "$h_1$" of the projections 21, forming a protective barrier for said projections 21 of the leaflets 13, which prevents the spread of pseudointima covering the sewing ring into the hinge mechanism that holds leaflets 13 within the valve body 1.

The first embodiment of the heart valve prosthesis shown in FIGS. 1 and 2 functions as follows. In the closed position the leaflets 13, which are interacting with the downstream surface 10 of the flange 8 of the annular body 1 by the support portions 24 of the projections 20 and the contact surfaces 14, close the orifice of the annular body 1 so as to restrict the blood backflow 5 through the prosthesis. At this moment due to excessive pressure jets 26 of the restricted blood backflow 5 are created which flow through the clearances between the portions 19 of the outer side surface 15 of the leaflets 13 and the inner surface 6 of the annular body 1. This provides the washing out of adherent blood elements in the zone where the leaflets 13 are hinged to the annular body 1 and thus preventing thrombus formation at the elements of the heart valve prosthesis. Furthermore, due to the definite shape and dimensions of the projections 20, the jets 26 of the blood backflow 5 at one of the portions 19 of said outer side surface 15 of the leaflets 13 reflect from the downstream support surface 10 of the flange 8 of the annular body 1 and move at an angle relative to the central axis 12 of the annular body 1. As a result a part of blood volume at the upstream end surface 2 of the annular body 1 begins to rotate in a certain direction thus eliminating stagnation zones and providing washing of the heart structures in front of the prosthesis.

When an excessive pressure is created from the side of the upstream end surface 2 of the annular body 1, the leaflets 13 interacting by the support portions 25 on the projection 21 with the upstream surface 9 of the flange 8, open to allow the passage of the direct blood flow 4.

At this moment the rotating blood volume generated by the jets 26 of the blood backflow 5 passing through the orifice of the annular body 1 turns the opening leaflets 13 to some angle around the central axis 12. This provides stable compulsory rotation of the leaflets 13 around the entire periphery of the inner surface 6 of the annular body 1.

At the same time the stagnation zone located at the region of hinges shall be washed by the blood backflow 5 through the clearances between the outer sid surface 15 of the leaflets 13 and the inner surface 6 of the annular body 1 as well as by the direct blood flow 4 because of the rotation of the leaflets 13 around the central axis of the annular body 1.

The direct blood flow 4 between the leaflets 13 is secured by forming parts 18 of the downstream surfaces 17 of the leaflets 13 smoothly concave.

When an excessive pressure is created from the side of the downstream end surface 3 of the annular body 1, the leaflets 13 interacting by the support portions 24 of the projections 20 with the downstream surfaces 10 of the flange 8 of the annular body 1, pivot into the closed position and restrict the blood backflow 5.

Provision of the smoothly convex support surfaces 2, 23 on the support portions 24 and 25 of the leaflets 13 ensures a rolling friction interaction thereof which leads to minimum wear of the interacting surfaces and better reliability and longer lifetime of the valve and in addition prevents trauma of the formed elements of blood.

Figure 3:
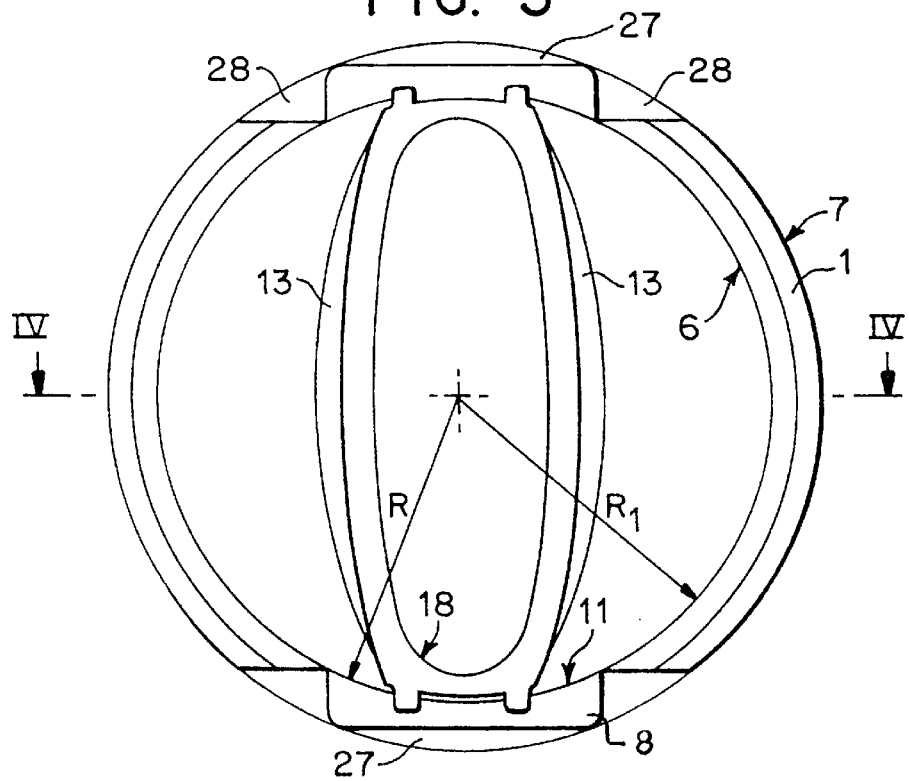
FIG. 3 is an enlarged view of a second embodiment of the heart valve prosthesis with its leaflets in an open position as viewed from the upstream side with respect to the direct blood flow.
Figure 5:
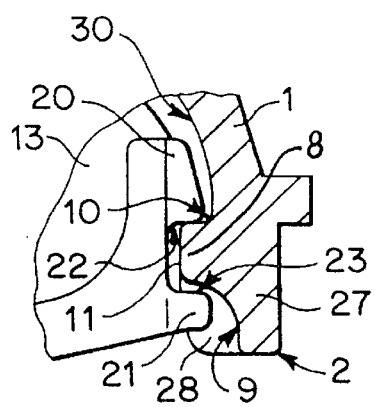
FIG. 5 is an enlarged fragmentary sectional view of the heart valve prosthesis taken along lines V—V of the heart valve of FIG. 4 in a closed position.

The second embodiment of the heart valve prosthesis shown in FIG. 3 to FIG. 5 comprises an annular body 1, having an upstream end surface 2 and a downstream end surface 3, facing the direct blood flow 4 and the blood backflow 5, respectively, an inner surface 6 and an outer surface 7.

In the interior of the annular body 1 an annular flange 8 is provided having an the upstream support surface 9, a downstream support surface 10, and a side surface 11, facing the central axis 12 of the annular body 1. The annular flange 8 runs along the entire periphery of the innner surface of the annular body 1.

The annular body 1 has two stepped protrusions 27 located on diametrically opposite portions of the upstream end surface 2 of the annular body 1, each of the protrusions having an upstream support surface 9 and a downstream support surface 10 facing the direct blood flow 4 and the blood backflow 5, respectively, and a side surface 11. The downstream support surfaces 10 of said stepped protrusions 17 lie higher upstream of the direct blood flow 4 than the upstream end surface 2, and the ends of the upstream support surfaces 9 thereof are provided with stops 28. The length of each upstream surface 10 between the stops 28 amounts between 0.05 to 0.25 of the length of the inner surface 6 of the annular body 1. In addition, the longitudinal axes 29 of the downstream support surfaces 10 of the stepped protrusions 27 are at an angle relative to the central axis 12 of the annular body 1. The values of the slant angles "β" of said longitudinal axes 29 of the downstream surfaces 10 of the stepped protrusions 27 located on diametrically opposite portions of the upstream end surface 2 of the annular body 1 are equal by modulus but with opposite sign. The side surfaces 11 of each stepped protrusion 27 face each other and their projections on the plane perpendicular to the central axis 12, are arcs of a circumference with its centre located on said central axis 12.

Within the annular body 1 two leaflets 13 are mounted so as to pivot between a closed position, restricting the blood backflow 5, and an open pasition enabling the passage of the direct blood flow 4. Each leaflet 13 has a contact surface 14 cooperating with the contact surface of the other leaflet 13 in the closed position, an outer side surface 15, an upstream surface 16 and a downstream surface 17 facing the direct blood flow 4 and the blood backflow 5, respectively. A part 18 of the downstream surface 17 of each leaflet is made concave to allow the passage of the direct blood flow 4 between the leaflets 13 in their open position. The outer side surface 15 of each leaflet 13 has two portions 19 formed with a clearance relative to the side surface 11 of the protrusions 27 of the annular body 1 and located on the opposite sides of the outer side surface 15 of the leaflets 13.

Each portion 19 has two projections 20 and 21 having an upstream surface 22 and a downstream surface 23, respectively, with two support portions 24 and 25, respectively, which interact with the corresponding downstream support surface 10 or upstream support surface 9 of the protrusions 27 of the annular body 1. The support portions 24 and 25 of the projections 20 and 21 are made smoothly convex. A part of the inner surface 6 of the annular body 1 extending from the side of the direct flow 4 is formed like a confuser surface 30 with which interact the projections 20 located on the portions 19 of the side surface 15 of the leaflets 13. The radius "R" of the side surfaces 11 of the stepped protrusions 27 is equal to the radius "$R_1$" of the inner surface 6 of the annular body 1.

The protrusions do not protrude inside the valve body 1. Therefore there is no reduction of the effective area of the body orifice, hence there are lower energy losses during the passage of direct blood flow 4 and better hemodynamic characteristics of the heart valve prosthesis.

The second embodiment of the heart valve prosthesis shown in FIGS. 3 to 5 functions like the prosthesis shown in FIGS. 1 and 2 with the exception that due to the action of forces from the side of the rotating part of the direct blood flow 4, because of the effects of the back flow jets 26, the opening leaflets 13 turn around the central axis 12 of the annular body 1 until the projections 21 interact with the stops 28 of the upstream surfaces 9 of the stepped protrusions 27. During valve closing the leaflets 13 skid along the slanting downstream support surface 10 due to pressure and at the same time also turn around the central axis 12 until the interaction of the projections 21 with the stops 28. The direction of the slant of the downstream support surfaces 10 of the stepped protrusions 27 is chosen in such a way that the leaflets 13 turn around the central axis 12 in one direction during valve opening and in the opposite one during valve closing.

In such a construction arrangement of the heart valve prosthesis the leaflets 13 also have an additional degree of freedom and can rotate around the central axis 12 of the annular body 1, not a full turn but only in the form of an oscillating movement. With such movement, the hinge mechanism zone also moves but the amplitude of this movement is limited by the stops 28 on the upstream support surfaces 9 of the stepped protrusions 27. Therefore surgeon gains the possibility to orientate the prosthesis in ventricle in such a way as to avoid the contact of the leaflets 13 with surrounding heart structures during valve opening.

Figure 6:
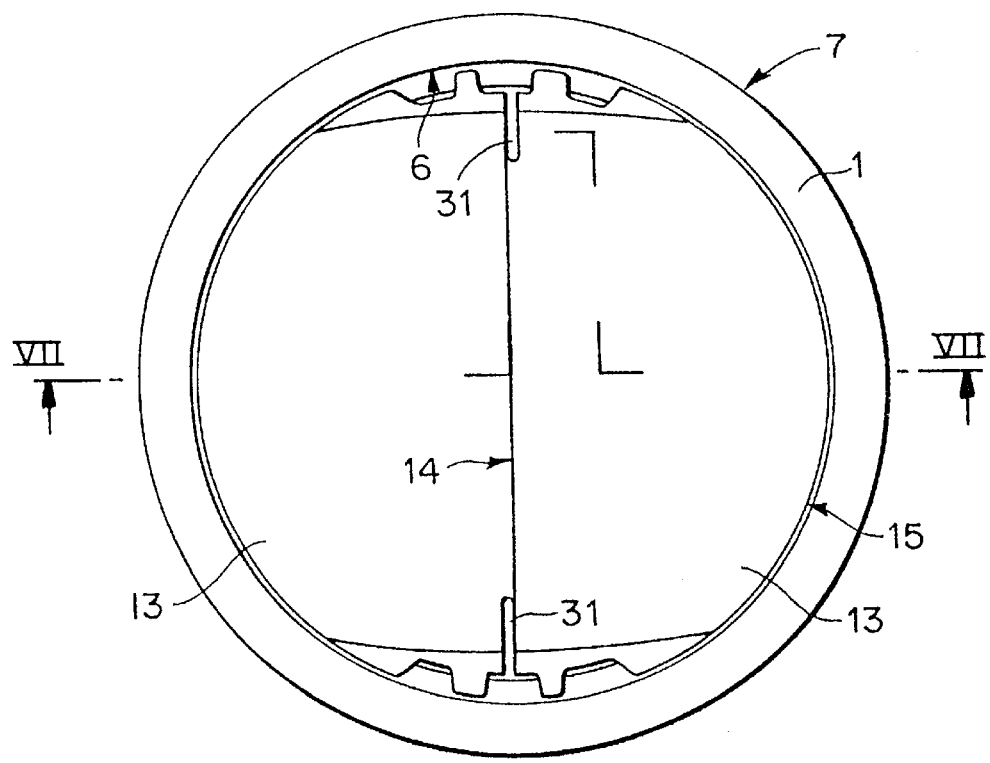
FIG. 6 is an enlarged view of a third embodiment of the heart valve prosthesis with its leaflets in a closed position as viewed from the downstream side with respect to the direct blood flow.

The third embodiment of the heart valve prosthesis shown in FIGS. 6 and 7 comprises an annular body 1, having an upstream end surface 2 and a downstream end surface 3, facing the direct blood flow 4 and the blood backflow 5, respectively, an inner surface 6 and an outer surface 7. Within the annular body 1 two leaflets 13 are mounted pivotable between a closed position in which the blood backflow 5 is restricted and an open position which enables the passage of the direct blood flow 4. Each leaflet 13 comprises a contact surface 14 cooperating with the contact surface of the other leaflet in the closed position, an outer side surface 15, an upstream surface 16 and a downstream 17 surface.

One channel 31 is provided on each leaflet 13, which crosses the contact surface 14 and is located on one side of the outer side surface 15. The channel 31 is limited on one side by the inner surface 6 of the annular body 1. The total area of said channels 31 and of the clearances between the outer side surface 15 and the inner surface 6 of the annular body 1 is chosen in such a way that the limited blood backflow will not not exceed 20% of the volume of the direct blood flow 4 and is from 0.2 to 8% of the orifice area of the annular body 1.

In such a construction arrangement of the prosthesis, the limited blood backflow 5 passing through the channels 31 when the leaflets 13 are in the closed position, washes the zones of the downstream surfaces 17 of the leaflets 13 where exists high probability of adhesion of the formed elements of blood. In addition the jets of the blood backflow 5, passing through the channels 31, reach the upstream end surface 2 of the annular body 1 and wash away the threads of fibrin which could spread from the surrounding heart structures to the side surface of the leaflets 13.

The laboratory studies have shown the minimal pressure losses across the heart valve prostheses made up in accordance with the invention during the passage of the direct flow of fluid with the optimum volume of back flow.

The tests at the accelerated life stand for a period equal to 50 years of in vivo service of the prosthesis have proved high durability and reliability of the prostheses. There have been no incident of disruption of the prosthesis. Wear of the interacting elements of the prostheses had been insignificant and hemodynamic and functional characteristics of the heart valve prostheses remained practically the same.

After the overall laboratory studies samples of the heart valve prosthesis made up in accordance with the invention have been submitted for the extended clinical tests, which provide high thromboresistance, hemodynamic effectiveness and reliability of the heart valve prostheses that follow the invention design for the replacement of damaged natural heart valves in humans.

EXAMPLE

Heart valve protheses as previously described are manufactured in six or more sizes with mounting diameters within a range of about 14–33 mm. For each prothesis, the following dimensions are applicable:

1) the width of the downstream surface 10 of the element 8 in the radial direction equals about 0.5–1 mm;

2) the form and the dimensions of concave part 18 of the leaflet 13 meet the condition that the three passage parts of the orifice have about the same area;

3) the clearances of portions 19 with the side surfaces 11 of the element 8 are within about the 0.05–0.25 mm range;

4) the clearances of the portions 19 with the inner surface 6 of the valve body 1 are within about 0.55–1.25 mm;

5) h is equal to about h1+(0.5–1.0) mm;

6) β is equal to about 10°; and 7) the width of channel 31 is within about 0.05–0.25 mm, and its length is from about 1/10 to 1/3 of the length of the contact surface 14 of the leaflet 13.

We claim:

1. A heart valve prosthesis comprising an annular body having an upstream end surface facing direct blood flow, a downstream end surface facing back blood flow, an inner surface and an outer surface, a support structure connected to said inner surface and projecting inwardly from said inner surface toward a central axis of said annular body, the support structure having an upstream support surface, a downstream support surface and a side surface facing the central axis of said annular body, and leaflets pivotally mounted to said annular body at hinge areas within said annular body so as to pivot between a closed position in which the back blood flow is restricted and an open position which allows the passage of the direct blood flow, each one of said leaflets having a contact surface of an other of said leaflets in the closed position, an outer side surface, an upstream surface, a downstream surface and support portions respectively interacting with said downstream support surface and said upstream support surface of said support structure of said annular body, wherein at least one portion of the outer side surface of at least one of said leaflets is formed at at least one of said hinge areas such that a clearance is provided between said at least one portion and said side surface of said support structure of said annular body and at said portion of said outer side surface, a downstream projection and an upstream projection are provided, an upstream surface of said downstream projection and a downstream surface of said upstream projection forming the support portions;

wherein in said closed position, said downstream projection and said clearance provide jets of restricted blood backflow which reflect from said downstream support surface and move at an angle relative to said central axis, so that said blood backflow rotates to eliminate blood stagnation zones in said prosthesis.

2. A heart valve prosthesis according to claim 1, wherein said at least one portion comprises two portions which are located on opposite sides of the outer surface of the leaflets.

3. A heart valve prosthesis according to claim 1, wherein the support portions are smoothly convex.

4. A heart valve prosthesis according to claim 1, wherein said support structure is arranged along the entire periphery of said annular body, at least a part of the downstream surface of each leaflet being smoothly concave to allow the passage of the direct blood flow between the leaflets in their open position.

5. A heart valve prosthesis comprising an annular body having an upstream end surface facing direct blood flow, a downstream end surface facing blood backflow, an inner surface and an outer surface, support means connected to said inner surface and projecting inwardly from said inner surface toward a central axis of said annular body, the support means having an upstream support surface, a downstream support surface and a side surface facing the central axis of said annular body, and leaflets pivotally mounted to said annular body at hinge areas within said annular body so as to pivot between a closed position in which the blood backflow is restricted and an open position which allows the passage of the direct blood flow, each one of said leaflets having a contact surface cooperating with a contact surface of an other of said leaflets in the closed position, an outer side surface, an upstream surface, a downstream surface and support portions comprising a downstream projection and an upstream projection respectively interacting with said downstream support surface and said upstream support surface of said support means of said annular body such that a clearance is provided between said support portions and said support means, wherein said downstream projection and said clearance provide jets of restricted blood backflow in the hinge areas of the leaflets when the leaflets are in the closed position, which jets reflect from said downstream support surface and move at an angle relative to said central axis, so that said blood backflow rotates relative to said central axis to eliminate blood stagnation zones in said prosthesis.

* * * * *